United States Patent
Nadeev et al.

(10) Patent No.: US 9,574,987 B2
(45) Date of Patent: Feb. 21, 2017

(54) METHOD FOR DETERMINING THE PROPERTIES OF POROUS MATERIALS

(71) Applicant: SCHLUMBERGER TECHNOLOGY CORPORATION, Sugar Land, TX (US)

(72) Inventors: Alexander Nikolaevich Nadeev, Spring, TX (US); Dmitry Alexandrovich Korobkov, Moscow (RU); Evgeny Mikhailovich Chuvilin, Moscow (RU); Sergey Sergeevich Safonov, Moscow (RU); Oleg Yurievich Dinariev, Moscow (RU)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 349 days.

(21) Appl. No.: 14/381,495

(22) PCT Filed: Feb. 22, 2013

(86) PCT No.: PCT/RU2013/000142
§ 371 (c)(1),
(2) Date: Aug. 27, 2014

(87) PCT Pub. No.: WO2013/129971
PCT Pub. Date: Sep. 6, 2013

(65) Prior Publication Data
US 2015/0107339 A1    Apr. 23, 2015

(30) Foreign Application Priority Data
Feb. 29, 2012  (RU) ................ 2012107572

(51) Int. Cl.
G01N 15/08  (2006.01)
G01N 25/48  (2006.01)
G01N 13/00  (2006.01)

(52) U.S. Cl.
CPC ........ G01N 15/088 (2013.01); G01N 25/4846 (2013.01); G01N 13/00 (2013.01)

(58) Field of Classification Search
CPC .................................................. G01N 15/088
(Continued)

(56) References Cited

U.S. PATENT DOCUMENTS 4,247,498 A * 1/1981 Castro ............... A01N 25/10
264/28
4,540,285 A * 9/1985 Amer ............... G01N 21/171
356/432
5,069,065 A * 12/1991 Sprunt ............... G01N 33/241
73/152.09

* cited by examiner

*Primary Examiner* — Laura Martin
*Assistant Examiner* — Alex Devito

(57) ABSTRACT

A sample of porous material is placed in a calorimeter cell and a pressure in the cell is increased starting from a pressure value of a first step by filling the cell with a wetting fluid. Measurements are taken of a heat flow to the cell and a fluid volume at each step. Then, the pressure in the cell is decreased to the pressure value of a first step with continued measurements of the heat flow to the cell. Increase and following decrease of the fluid pressure in the cell are repeated at least once. Then a temperature in the cell is decreased below a wetting fluid crystallization point. Once the fluid has been fully crystallized in sample pores, the temperature in the cell is increased above a wetting fluid melting point. Wetting limiting angle of the pores filled with fluid, and pore sizes are determined based on the results of heat flow measurements with due consideration of heat effect of fluid compression.

6 Claims, 2 Drawing Sheets

METHOD FOR DETERMINING THE PROPERTIES OF POROUS MATERIALS

CROSS-REFERENCE TO RELATED APPLICATIONS

This application is the U.S. National Stage Application under 35 U.S.C. §371 of International Patent Application No. PCT/RU2013/000142 filed Feb. 22, 2013, which claims priority to Russian Application No. 2012107572 filed Feb. 29, 2012, both of which are incorporated herein by reference in their entireties.

FIELD OF THE DISCLOSURE

The disclosure relates to the studies of porous materials, specifically, to methods for determining wettability and pore size distribution.

BACKGROUND

Wettability is an important phenomenon significantly impacting fluid distribution and dynamics in porous media. Specifically, in order to find solutions to multiple research and engineering problems in the petroleum industry rock characteristic properties need to be determined, including mineral composition, pore volume structure, and pore surface wettability. These are the key properties for understanding oil and gas formations and simulating fluid flow properties: phase permeability, displacement factor, etc. Changes in free surface energy associated with rock/fluid interface result in heat emission or absorption. The heat effect value is a function of specific surface and pore volume wettability. In endothermic processes, such as most phase transitions, heat is absorbed.

The conventional approach to core wettability determination is the Amott method and its modifications (See, for instance, J. C. Trantham, R. L. Clampitt, Determination of Oil Saturation After Waterflooding in an Oil-Wet Reservoir—The North Burbank Unit, Tract 97 Project, JPT, 491-500 (1977)). The Amott method is based on the fact that a wetting fluid can spontaneously saturate a rock core displacing a non-wetting fluid. The main disadvantage of the Amott method is a big error in core analysis both of neutral wettability samples and small-sized samples (less than 1 inch).

Nuclear Magnetic Resonance (NMR) is also a core analysis method used to determine pore size distribution (U.S. Pat. No. 4,291,271). The method is based on determining fluid distribution in the core and could only give indirect evidence of rock sample wettability.

The results of calorimetric studies have been increasingly used lately in determining properties of porous materials. Calorimetric methods can be used to study solid/liquid interfaces. The Differential Scanning calorimetry (DSC) can measure heat effects caused by phase transitions, changes in the system inner energy, and chemical reactions as a function of temperature. In DSC a difference between heat flow to a sample and a reference at the same temperature is recorded as a function of temperature. The reference may be an inert material such as alumina, or just an empty cell (International Standard ISO 11357-1, Plastics—Differential Scanning calorimetry (DSC), First edition 1997 Apr. 15). The heat effect may be either positive or negative. In most phase transitions, heat is absorbed. Therefore heat flow to the sample is higher or than that to the reference. Hence, the difference is positive.

SUMMARY

The method provides for a higher accuracy of property determination and a broader range of pore sizes covered (including micro-pores), which is achieved through determination of wettability and pore sizes from two physical/chemical processes: fluid penetration into a porous medium and a shift in phase transition temperature (solid/liquid) in a porous medium.

Method for determining properties of porous materials comprises placing a sample of a porous material into a calorimetric cell and step by step increasing a hydrostatic pressure in the calorimetric cell with the sample by filling the cell with a wetting fluid and keeping till stabilization of a heat flow at each step. Then, the heat flow to the calorimetric cell and a volume of fluid at each step is measured. The hydrostatic pressure of the wetting fluid in the calorimetric cell is decreased to pressure value of a first step with continuous measurement of heat flow to the cell. At least once step by step increase and following decrease of the fluid pressure in the calorimetric cell down to the pressure value of the first step are repeated.

Then a temperature of the calorimetric cell is decreased at constant hydrostatic pressure below a crystallization point of the wetting fluid with continuous measurement of heat flow and fluid volume. After completion of fluid crystallization in pores of the sample the temperature of the calorimetric cell is increased above a melting point of the wetting fluid with continuous measurement of heat flow and fluid volume. Contact angles and pore size distribution of sample pores filled with the wetting fluid are determined based on results of heat flow measurement and taking into account a heat effect from fluid compressibility.

The heat effect of fluid compression may be taken into account with the help of a basic pre-test in which the wetting fluid is filled into the cell containing no sample, then, a hydrostatic pressure in the calorimetric cell is increased step by step starting from a first step and then decreased to the value of the first step with measurement of heat flow into the cell. In the process, measurements are taken of the heat flow to the cell.

BRIEF DESCRIPTION OF THE DRAWINGS

The invention is illustrated by drawings, where.

DETAILED DESCRIPTION

Figure 1:
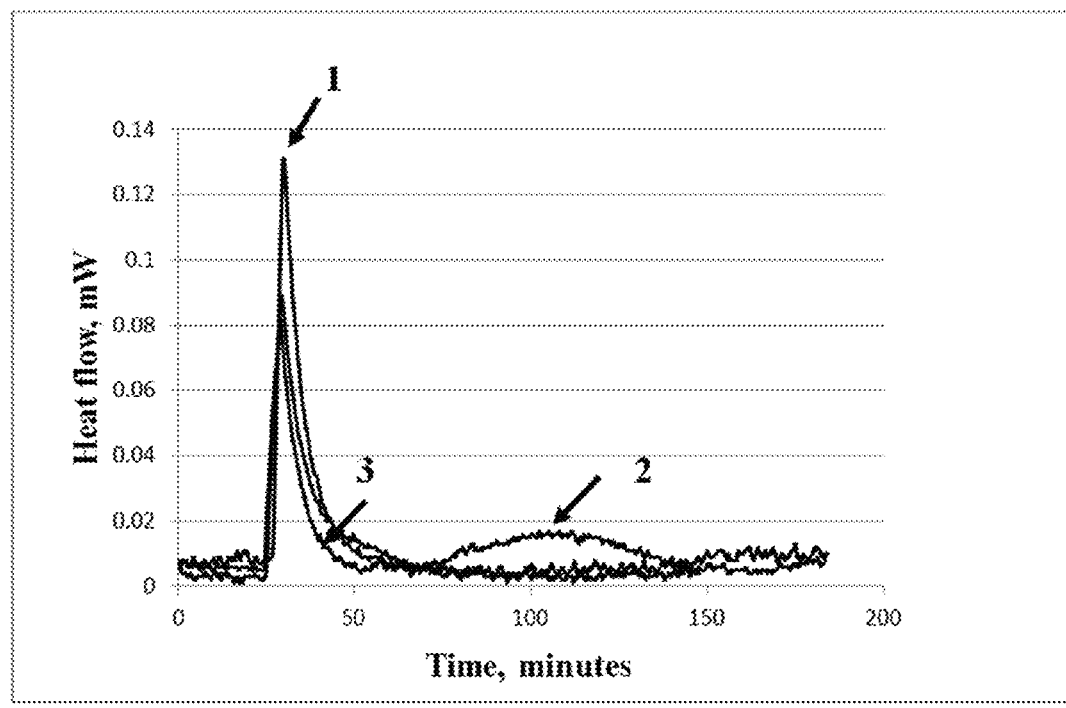
FIG. 1 shows a heat flow as a time function while brine is penetrating into sandstone.

The proposed method for determining properties of porous materials is based on heat flow measurements by micro-calorimetric methods in the process of fluid (water, solution or oil) penetration into a porous rock structure (sandstone, limestone, etc.), and subsequent crystallization/melting in a pore volume.

The novelty of the method is based on determining a value of temperature shift in a heat effect associated with phase transition (for instance, ice/water) in sample pores, and a heat effect from wetting associated with fluid (for instance, water) injection.

In case of the simplest system—a drop of fluid on a homogeneous, flat and inert surface—a limiting angle is determined from the Young equation:

$$\gamma_{sv} = \gamma_{sl} + \gamma_{lv} \cos \theta, \qquad (1)$$

where θ—a contact angle, $\gamma_{sv}$—a surface energy at the solid/vapor interface, $\gamma_{sl}$—a surface energy at the solid/liquid interface, $\gamma_{lv}$—a surface energy at the liquid/vapor interface.

It is known that a temperature shift associated with substance melting/solidification phase transition depends on size of particles. If a given phase transition takes place in a porous body where the size of particles is limited by size of pores, the temperature shift will characterize pores of a rock sample. So, fluid melting temperature in bulk $T_0$ and in a porous structure $T_m$ can be measured by a micro-calorimeter. The temperature shift associated with phase transition and dependent upon the pore size may be calculated by the Gibson-Thompson formula. Notably, a non-freezing liquid layer should be considered in calculations (0.5-2 nm). That correction is especially important in analyzing samples with nanopores:

$$\Delta T_m = T_0 - T_m = \frac{2T_0 \gamma_{sl} v_l}{(R-t) \cdot \Delta H} = \frac{2T_0 \gamma_{sl} v_l}{r_{eff} \cdot \Delta H} \quad (2)$$

$\gamma_{sl}$—a surface energy at a solid/liquid (ice/water) interface, $v_l$—a liquid molar volume, R—pore size, t—a non-freezing liquid layer, $r_{eff}$—an effective pore radius, $\Delta H$—a phase transition enthalpy.

With fluid penetrating into a porous medium, the process of surface/liquid interface starts under controlled pressure. Variation in free energy values ($\Delta F$ of area unit) can be described by the following equations (3, 4):

$$\Delta U = \Delta F - T \frac{\partial \Delta F}{\partial T} \quad (3)$$

$$\Delta F = \gamma_{sl} - \gamma_{sv} \quad (4)$$

where $\Delta U$—change in the system inner energy in response to fluid penetration.

Using the Young equation (1) and energy variation, the limiting angle can be expressed as:

$$\Delta U = -\gamma_{lv} \cos\theta + T \frac{\partial \gamma_{lv} \cos\theta}{\partial T} = \left(-\gamma_{lv} + T \frac{\partial \gamma_{lv}}{\partial T}\right) \cos\theta + T \frac{\gamma_{lv} \partial \cos\theta}{\partial T} \quad (5)$$

Equation (5) can be approximated to (6) when the limiting angle is not controlled by temperature.

$$\cos\theta = \frac{-\Delta U}{\left(\gamma_{lv} - T \frac{\partial \gamma_{lv}}{\partial T}\right)} \quad (6)$$

The advantage of calorimetric methods is an option for conducting experiments in which the system initial and finite states are well-defined, which is not always the case with other methods, like conventional methods for determining contact angle.

The proposed method is used as follows. A cell containing a sample is placed in a calorimeter, for instance BT2.15 (SETARAM, France, http://www.setaram.ru/BT-2.15-ru.htm). Then the cell is filled with a wetting fluid (oil, water, salt solution) at a constant flow rate until a hydrostatic pressure exceeds atmospheric pressure, for instance, 0.1 MPa (1 bar). A time needed for heat flow stabilization is a function of a flow rate and temperature of the wetting fluid filling the calorimeter cell (usually, several hours). Then, the hydrostatic pressure is increased step-by-step. A size of a pressure step depends on specifics of the sample pore volume, an amount of macro- and micro-pores. In our case, the pressure change steps were as follows: 0.2 MPa (2 bar), 0.4 MPa (4 bar), 0.8 MPa (8 bar), 1.0 MPa (10 bar), and 2.0 MPa (20 bar). The sample is held at each pressure step for several hours for stabilization of the heat flow. While increasing the pressure the heat flow to the cell is measured, i.e., the number of mW/sec (FIG. 1), and a volume of the fluid injected into the sample-containing cell.

Then, the fluid pressure is reduced to 0.1 MPa (1 bar), and the system is kept until the heat flow is stabilized. Then, at least once step by step increase and following decrease of the fluid pressure in the calorimetric cell down to value of the first step are repeated.

At the next stage, fluid pressure is stabilized at a certain value, for instance, 0.1 MPa (1 bar). Meanwhile, the sample remains filled with fluid. Then, the temperature of the cell with the sample is decreased at constant pressure. An important parameter for determining pore size distribution in the sample is a phase transition temperature at which fluid would crystallize. For instance, crystallization temperature for water solutions in bulk is somewhere around 0° C., depending on salts dissolved in them. If water solution is injected in the experiment at temperature above crystallization point, than, at that stage, the temperature is decreased below water solution crystallization point. In the solid/liquid phase transition, change in the fluid volume depending on the sample temperature is measured, as well as heat flow.

Then, after full fluid crystallization, the temperature is raised above the melting point of that fluid. While raising the temperature, the heat flow and change in the fluid volume are measured.

At each step of increasing and decreasing the pressure, a heat effect of sample wetting by the fluid is measured, and it is necessary to consider the heat effect of the injected fluid compression. Further, a wetting contact angle is calculated, for instance, by formula (6). Formula (6) may be simplified for the purpose of wetting angle calculation assuming that surface energy ($\gamma_{lv}$) does not change in the temperature range in question. Then the formula is simplified and the limiting angle can be calculated from the ratio of the system inner energy change ($\Delta U$) to surface energy $$\cos\theta = \frac{-\Delta U}{\gamma_{lv}} \quad (7)$$

By integrating the heat flow over time at a given hydrostatic pressure (FIG. 1) and deducting the heat effect of fluid compression (FIG. 1, Peak 1) we obtain the value of the system inner energy change from wetting ($\Delta U$). Surface energy value $\gamma_{lv}$ can be calculated by multiplying tabular reference value of fluid surface tension (A. P. Babichev, N. A. Babushkina, A. M. Bratkovsky et al., Physical Values: Manual, Moscow, Energoatomizdat, 1991, p. 1232) and the sample specific surface. Sample specific surface can be measured, for instance, by gas adsorption method (Stephen Brunauer, P. H. Emmett, Edward Teller, J. Am. Chem. Soc., 1938, 60 (2), pp 309-319).

Figure 2:
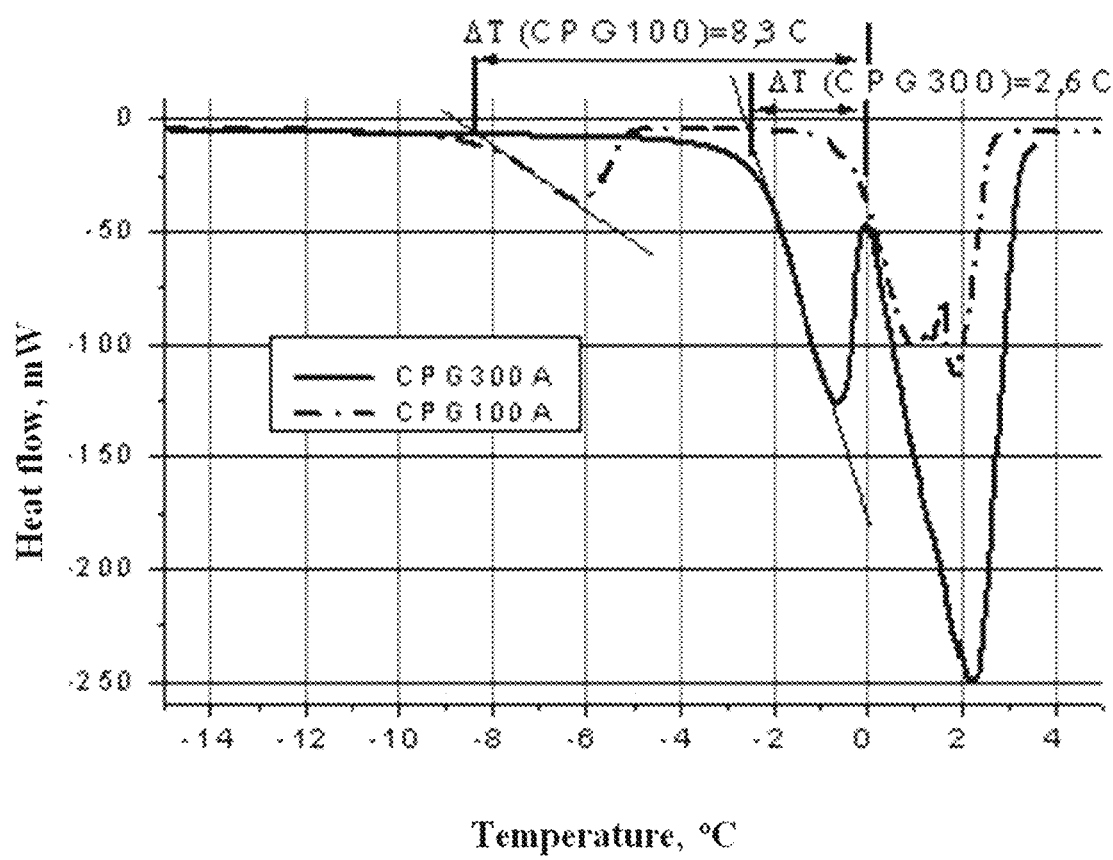
FIG. 2 shows ice/water phase transition in a sample with known pore sizes.

Measured temperature shifts in sample pores associated with phase transition (liquid/solid) relative to a typical phase transition temperature in a void space (FIG. 2, peaks around −6° C. and −1° C.) may be used to determine pore sizes, for instance by formula (2). Fluid melting temperature in bulk is $T_0$, and $T_m$ is the difference between fluid melting temperature in pores and in bulk, i.e., between peak values (FIG. 2). Both values are determined from experiment. Surface tension at solid/liquid interface ($\gamma_{sl}$, ice/water in our case), fluid molar volume ($v_l$), and phase transition enthalpy ($\Delta H$) are tabular reference values (A. P. Babichev, N. A. Babushkina, A. M. Bratkovsky et al., Physical Values: Manual, Moscow, Energoatomizdat, 1991, p. 1232). Using said values, pore sizes can be determined for each temperature shift (difference) Tm. Then, pore volumes and typical pore sizes as measured are used to determine pore size distribution for a given sample.

FIG. 1 relates to brine injection into a sandstone sample under a pressure of 1.0 MPa (10 bar); heat flow functional connection with time is shown under fluid pressure of 10 bars: reference experiment 1, fluid injection—2, and repeated fluid injection—3.

The major narrow peak represents heat emission from fluid compression, and heat flow value is a function of pressure change value. Additional heat effects observed after pressure stabilization, for instance, the heat flow wide peak (FIG. 1, indicated by arrow) are associated with brine injection into the sample pore volume. Heat effects associated with brine injection are observed under other pressure values as well, for instance, 0.8 MPa (8 bar). Heat effect value, i.e., wetting heat value is used to determine the limiting angle ($\theta \approx 45°$) by formula (6). The resulting contact angle is in good agreement with the Ammot-Harvey index measured for that sample independently.

Samples made by Asahi Company and used in earlier experimental calorimetric studies of ice/water phase transition (CPG100A and CPG300A) were taken for reference as samples with known pore sizes. Water melting temperature in pores was measured in compliance with the ISO 11357-1 Standard. Additional heat flow peaks occurring below water freezing point were observed in both CPG samples (FIG. 2). Temperature shift in phase transition depends on the size of pores. Considering that $v_l$, and $\Delta H$ values for water and surface tension at the ice/water interface ($\gamma_{sl}$=60.5 mJ/m2) are provided in reference tables, pore sizes can be calculated for the CPG samples (Formula 2). As follows from the calculation, the effective pore radius for CPG 100A ($r_{eff}$=120 Å); for CPG300A, ($r_{eff}$=380 Å). Those data show good correlation with pore sizes indicated by manufacturer.

The invention claimed is:

1. A method for determining properties of porous materials comprising:
    placing a sample of a porous material into a calorimetric cell,
    increasing step by step a hydrostatic pressure in the calorimetric cell with the sample starting from a pressure value of a first step by filling the cell with a wetting fluid and keeping until stabilization of a heat flow at each step,
    measuring the heat flow to the calorimetric cell and a volume of fluid at each step,
    decreasing the hydrostatic pressure of the wetting fluid in the calorimetric cell down to the pressure value of the first step with continuous measurement of the heat flow to the cell,
    at least once repeating step by step increase and following decrease of the fluid pressure in the calorimetric cell down to the pressure value of the first step,
    decreasing a temperature of the calorimetric cell at constant hydrostatic pressure below a crystallization point of the wetting fluid with continuous measurement of the heat flow and the fluid volume,
    after completion of fluid crystallization in pores of the sample increasing the temperature of the calorimetric cell above a melting point of the wetting fluid with continuous measurement of the heat flow and the fluid volume,
    calculating contact angles and pore size distribution of the pores of the sample filled with the wetting fluid based on results of heat flow measurement and taking into account a heat effect from fluid compressibility.

2. The method of claim 1 wherein the wetting fluid is preliminary filled into the calorimetric cell without the sample, the hydrostatic pressure in the calorimetric cell without the sample is increased step by step starting from a pressure value of a first step and then decreased to the value of the first step with measurement of heat flow into the cell.

3. The method of claim 1 wherein the pressure value of the first step is 0.1 MPa (1 bar).

4. The method of claim 1 wherein the wetting fluid is oil.

5. The method of claim 1 wherein the wetting fluid is water.

6. The method of claim 1 wherein the wetting fluid is a water based solution of salt.

* * * * *